United States Patent
Gielen

(10) Patent No.: US 6,484,059 B2
(45) Date of Patent: Nov. 19, 2002

(54) METHOD FOR OPTIMIZED BRAIN STIMULATION FOR TREATING MOVEMENT DISORDERS

(75) Inventor: Frans L. H. Gielen, Eckelrade (NL)

(73) Assignee: Medtronic, Inc., Minneapolis, MN (US)

( * ) Notice: Subject to any disclaimer, the term of this patent is extended or adjusted under 35 U.S.C. 154(b) by 8 days.

(21) Appl. No.: 09/799,709

(22) Filed: Mar. 7, 2001

(65) Prior Publication Data

US 2001/0008972 A1 Jul. 19, 2001

Related U.S. Application Data

(62) Division of application No. 09/186,490, filed on Nov. 5, 1998, now Pat. No. 6,253,109.

(51) Int. Cl.[7] ................................................ A61N 1/36
(52) U.S. Cl. ......................... 607/45; 607/48; 600/595
(58) Field of Search ............................. 607/48, 45, 2; 128/898, 899; 600/544, 545, 595, 554

(56) References Cited

U.S. PATENT DOCUMENTS

| 3,825,015 A | | 7/1974 | Berkovits ................... 128/404 |
| 4,245,645 A | | 1/1981 | Arseneault et al. ......... 128/642 |
| 4,735,205 A | | 4/1988 | Chachques et al. ... 128/419 PG |
| 5,713,922 A | * | 2/1998 | King .............................. 607/2 |
| 5,735,885 A | * | 4/1998 | Howard et al. ............... 607/55 |
| 6,011,996 A | | 1/2000 | Gielen et al. |
| 6,027,456 A | * | 2/2000 | Feler et al. .................. 600/554 |
| 6,066,163 A | * | 5/2000 | John ............................ 607/45 |
| 6,405,079 B1 | * | 6/2002 | Ansarinia ...................... 607/2 |

* cited by examiner

*Primary Examiner*—Kennedy Schaetzle
(74) *Attorney, Agent, or Firm*—Thomas F. Woods; Eric R. Waldkoetter; Tom G. Berry

(57) ABSTRACT

There is provided apparatus and a method for testing to optimally place a deep brain lead, particularly for stimulating the GPi or other deep brain target to treat neurological disorders such as Parkinson's Disease and the like. The invention embraces determining the location of a feedback target such as the motor cortex, the location of the deep brain target, and inserting a test lead along a substantially linear trajectory so as to be able to stimulate both concurrently. The test lead has an electrode at about its distal end for stimulation of the deep brain target, and an electrode adjustably positioned 3–8 cm proximal for stimulation of the motor cortex. When stimulation is applied concurrently through both electrodes, the affected body portion, e.g., limb, can be made to move when and if the deep brain electrode is optimally positioned. The position can be checked during surgical implant of the system, and the lead position adjusted until the optimum position is found. By use of this invention, the best lead position for the permanently implanted lead can be determined during the surgical procedure.

9 Claims, 3 Drawing Sheets

METHOD FOR OPTIMIZED BRAIN STIMULATION FOR TREATING MOVEMENT DISORDERS

This divisional patent application corresponds to and claims the benefit of the filing date of parent U.S. patent application Ser. No. 09/186,490 filed Nov. 5, 1998 for "System and Method for Optimized Brain Stimulation" to Frans Gielen, now U.S. Pat. No. 6,253,109.

FIELD OF THE INVENTION

This invention lies in the field of systems for brain stimulation and recording of brain activity and, more particularly, systems for placement of the lead for stimulating and/or recording at an optimized physiological brain target, for the treatment of conditions such as movement disorders.

BACKGROUND OF THE INVENTION

Deep Brain Stimulation (DBS) has been found to be successful in treating a variety of brain-controlled disorders, including movement disorders. Generally, such treatment involves placement of a DBS type lead through a burr hole drilled in the patient's skull, followed by placement of the lead and then applying appropriate stimulation through the lead to the physiological target. The placement portion of the treatment is very critical, and has been the subject of much attention and research. In particular, finding the deep brain target and then placing the permanent lead so that it efficiently stimulates such target is very important. See, for example, U.S. patent application Ser. No. 09/009,247, filed Jan. 20, 1998, Gielen et al, which deals with the localization procedure in functional stereotactic brain surgery, i.e., the initial probing to find the optimum site for delivering the stimulation.

Finding the optimal physiological target in deep brain stimulation implants for the treatment of movement disorders is a particularly complicated task. This is especially true for the treatment of symptoms which cannot be tested at the operating table during lead implant. For instance, it is impossible to test walking and postural stability in Parkinson's Disease (PD) patients during DSB lead implant. Two other major PD symptoms, Rigidity and Akinesia, are also considered difficult to evaluate quantitatively during DBS lead implant. Thus far, no reliable quantitative evaluation procedures exist that can be performed during the surgical DBS implant procedure for these major symptoms.

A recent procedure has been suggested which allows post-operative quantitative testing of muscle function in PD. See Pascual-Leone, Rapid Rate Transcranial Magnetic Stimulation (rTMS) in Movement Disorders; Movement Disorders, Vol 11, Suppl. #1, pp.:23, 1966. In this procedure, trans-cranial magnetic stimulation of the motor cortex is used to show that the brain is able to control muscle movements in a normal way when and if the DBS electrode is implanted in the optimal physiological position in the Globus Pallidum Internae (GPi) and electrical stimulation with the appropriate parameters is applied through the DBS electrode. Thus, it was shown that those areas of the motor cortex (MC) which are involved in the control of movement in the muscle of the thumb can only be activated if the appropriate DBS stimulation is concurrently applied to the correct part of the GPi.

Based on this finding, it is reasonable that an improved procedure could be utilized for optimizing the implant position of the DBS electrode(s) in the GPi or other neuro-modulation target for treating disorders, and particularly movement disorders, by means of deep brain stimulation. Thus, if postural instability of the patient is a major PD symptom, one might be able to find the optimal physiological target for the DBS electrode by seeing when trans-cranial magnetic stimulation of the motor cortex achieves optimal control movement of the leg muscles. However, this magnetic stimulation procedure is not suitable for intra-operative use, i.e., for testing lead position while the lead is stereotactically held. The applied very fast changing and very strong magnetic fields may interact with the DBS electrode in a comparable way as suggested for MRI imaging procedures, which is contra-indicated for DBS patients. Further, the trans-cranial magnetic stimulation coil cannot be accessed to the relevant sites of the brain when the DBS lead is being held by the stereotactic equipment. This means that the Leone procedure is not directly suggested for use in evaluating the excitability of the relevant motor cortex areas during lead implant. Thus, while the prior art procedure is appropriate for certain postsurgical testing because it is non-invasive, it is not suggested for intra-operative use.

The continued need in the art is a system and procedure that can be utilized during surgery when the DBS lead is being implanted, to determine when it has been placed in the optimal position for stimulation therapy of the patient's particular disorder, or for recording of brain activity. In general terms, the aim is a system and method for stimulation of the GPi or other neuro-stimulation target, and a feedback target such as the MC. A key to this invention is the recognition that during surgery, there is no need for a non-invasive way of stimulating the feedback target. The invention, rather, provides apparatus and a method of testing for the optimal DBS electrode position during the invasive surgery, and as part of the localization test procedure that is required in any event, enabling a reliable determination of optimal lead placement before permanent lead implant and close of surgery.

SUMMARY OF THE INVENTION

A primary object of this invention is to provide a system, and procedure, for determining with a test lead or permanent lead when a brain electrode is positioned optimally so during stimulation of the brain target normal patient excitability of a feedback target such as the motor cortex achieves the desired result, e.g., the desired body movement of a patient with a movement disorder. Alternately, another object is to provide an improved capacity to record brain activity.

The invention takes advantage of the fact that during DBS lead implant, the patient's brain is already subject to an invasive procedure. This being the case, both the neuro-modulation target and the feedback target can be readily stimulated during surgery. Thus, in the case of movement disorders involving the motor cortex, the stimulation of the motor cortex concurrently with the GPi need not be limited to a non-invasive technique.

In order to achieve the above objects, the invention provides for a lead system, preferably just one lead, which is inserted on a trajectory which passes in one dimension through the motor cortex or other feedback target, and proceeds to the GPi or other neuro-modulation target. The lead has conventional DBS electrodes for stimulating the DBS target, and also has an electrode positionable so that stimuli can be delivered to the feedback target while the DBS target is being stimulated. By varying the position of the DBS electrodes, and repeatedly stimulating both the DBS target and the feedback target, and observing the relevant patient body movement or other reaction, the optimal DBS target location can be found. Also, either or both of the electrodes can be used for recording brain activity.

After the finding of the optimal DBS target location, the test lead is removed and a permanent lead positioned so that the DBS electrode(s) is located at the optimal target position. The permanent lead also preferably is aligned along the linear trajectory which includes both the neuro-modulation and the feedback targets, and carries electrodes for stimulating or recording at both targets, thereby enabling post-operative testing. The system includes a generator device with dual stimulus pulse channels for providing stimuli with appropriate parameters for stimulating the respective targets, and sense channels for amplifying and processing detected brain signals.

BRIEF DESCRIPTION OF THE DRAWINGS

FIG. 4 is a flow diagram illustrating the primary steps taken in using the system of this invention to determine whether and when the brain lead has been optimally positioned in a patient's brain in order to treat a movement disorder or the like.

DETAILED DESCRIPTION OF THE PREFERRED EMBODIMENTS

Figure 1:
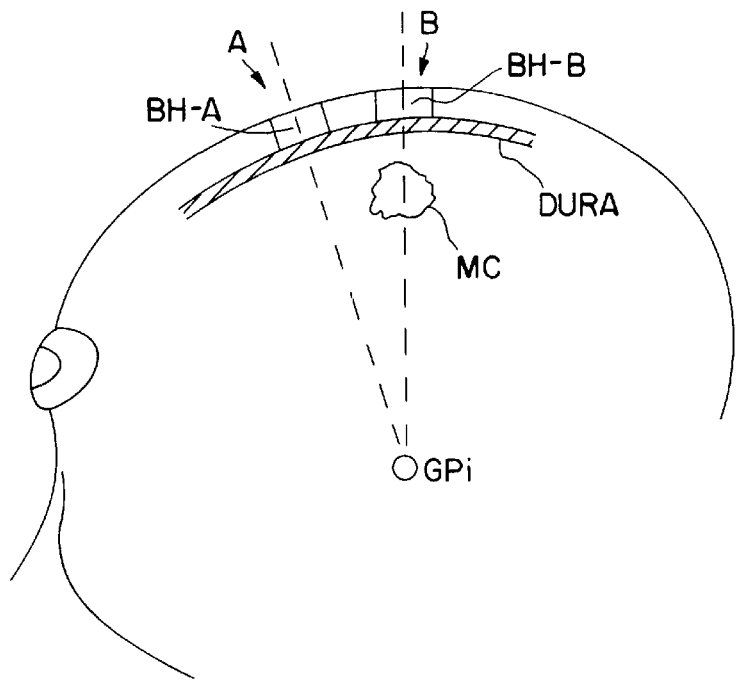
FIG. 1 is a diagrammatic view of a patient's skull and the target path or paths taken to stimulate target areas of the brain in accordance with this invention, and/or to record brain activity at the dual target sites.

Referring now to FIG. 1, there is shown a diagram of a patient's head, with burr holes BH-A and BH-B shown drilled through the patient's skull to allow entry beneath the dura. While FIG. 1 presents an illustration of the specific MC/GPi embodiment, it is to be understood that the principles involved are equally applicable to other targets, as discussed above. A normal trajectory would be that indicated through the hole BH-A, along trajectory A, to the GPi. However, as indicated, the motor cortex MC is not along this line. In order to have a single one-dimensional trajectory which will involve both the GPi and the MC, burr hole BH-B is utilized, to provide a trajectory as indicated along indicated line B. It is to be noted that skull sizes vary from patient to patient, and that accordingly the distance from the GPi target and the MC target will be variable, perhaps in the range of up to 2 cm from patient to patient. For this reason, the lead of this invention preferably includes an adjustable electrode location for stimulating the feedback target, e.g., the MC, when the distal electrodes are in place for stimulating the GPi or other brain target.

Figure 2:
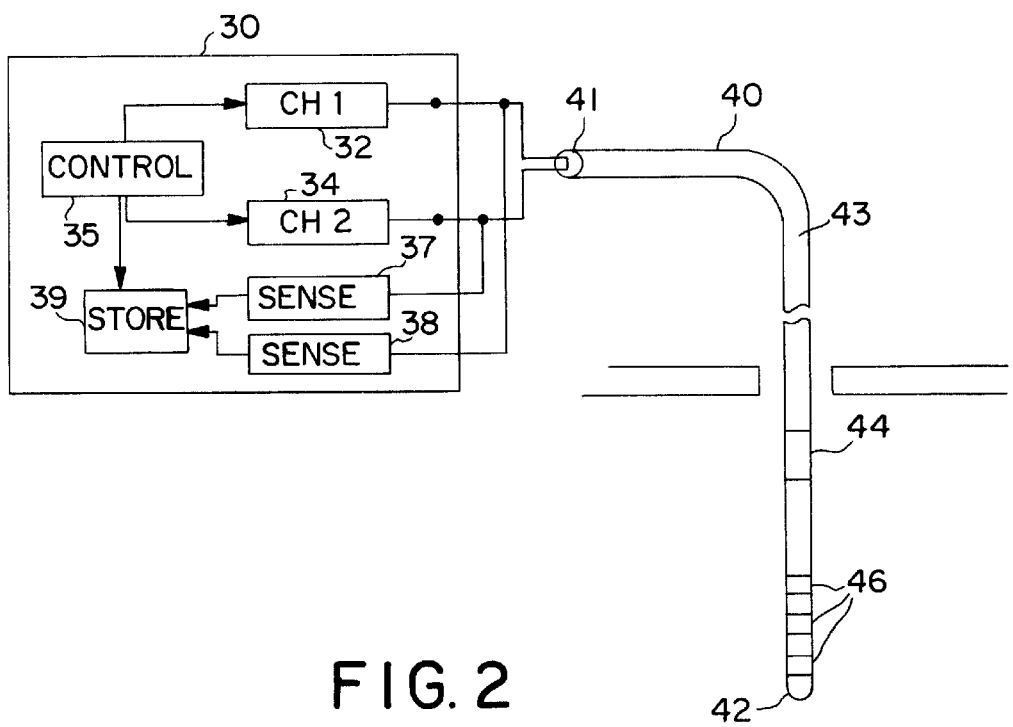
FIG. 2 is a schematic diagram showing a system in accordance with this invention, including an implantable stimulator/recorder device, and a test or premanent lead designed to enable dual stimulation of different brain sites and/or recording of brain signals from such sites.

Referring now to FIG. 2, there is shown a diagram of a stimulator/recorder device 30 coupled to and used in connection with a lead 40. Stimulator device 30 may be, for example, a Medtronic Model 3628, or a modification thereof; and the lead may be a modification of Medtronic InterStim Model 4300 or Medtronic DBS Lead Model 3387. As indicated, the stimulator device contains two pulse generation channels, channel 1 indicated at 32 and channel 2 at 34. Each of these channels is controlled by control block 35, which may appropriately utilize a microprocessor and/or other control and timing circuitry. The lead proximal end 41 is connected to the outputs of the device 30. Channel 1 connects to one or more lead conductors which provide electrical connection to distal electrodes indicated at 46 near the lead distal end 42. These electrodes are positioned at the neuro-modulation target, e.g., the GPi. The pulses generated by channel 1 and delivered to the deep brain location are, for example, pulses of 60–120 $\mu$S pulse width, typically delivered at a rate in the range of about 50–250 Hz, and with a pulse amplitude of about 1–10 v. The signals delivered by channel 2 are connected through to electrode 44, which is shown positioned proximally from electrodes 46, and at a distance in the neighborhood of 3–8 cm from the distal electrodes 46, depending on the application. For example, for the MC/GPi embodiment, the positioning of electrode 44 is designed to place it proximate to the motor cortex when the distal electrodes 46 are positioned at the GPi brain target. The pulses delivered by channel 2 are, e.g., pulses of a width 1–10 ms, delivered at a rate of 1 to 5 Hz and with a voltage in the range of 1–10 v. Signals received from the electrodes are processed at sense channels 37,38 and stored at 39.

Figure 3A:
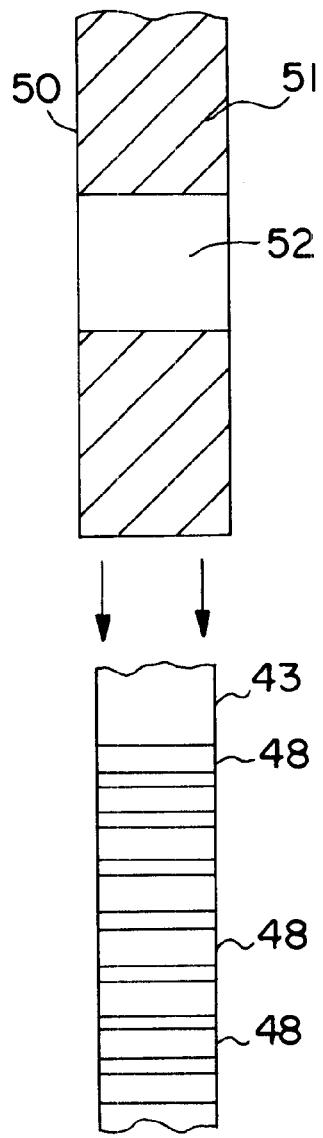
FIG. 3A is a diagrammatic view showing a brain stimulating lead and a slidable sleeve with a window.
Figure 3B:
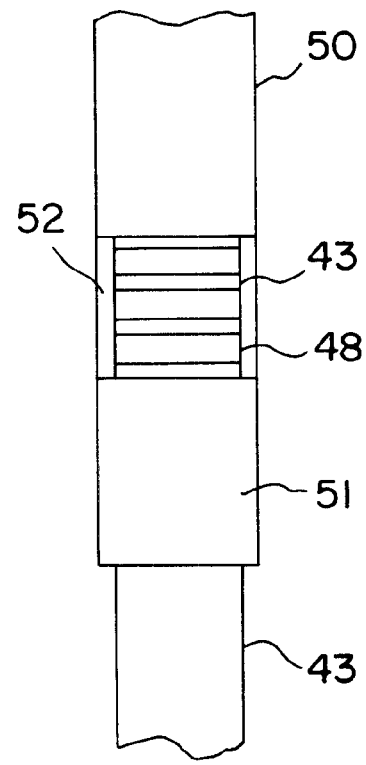
FIG. 3B is a diagrammatic view showing the sleeve in position over the lead portion which carries electrodes for stimulating the motor cortex, thereby enabling adjustment of the location of an effective electrode on the lead for stimulating the motor cortex at the same time that the physiological brain target is stimulated.

Referring now to FIGS. 3A and 3B, there is shown one arrangement for adjusting the position of electrode 44, to provide for stimulation of the MC concurrently with stimulation of the GPi. In this embodiment, electrode 44 is suitably comprised of a series of smaller ring electrodes, as indicated at 48, the purpose of this design being to achieve a greater lead flexibility. Alternately, but at the cost of some flexibility, the electrode 44 may be one integral ring electrode, providing a large surface extending around the tubular body 43 of lead 40. Shown above the lead portion carrying electrode 44 is a sliding tubing, or sleeve 50, being a hollow tubing having an inner diameter adapted to just fit over the outer diameter of lead body 43. Tubing 50 is made of an electrically insulative material coating 51, except at a window portion 52 of predetermined length. The tubing 50 extends proximally a sufficient distance so that it can be manipulated, i.e., slid along the lead 43 so as to position the window portion 52 relative to the lead. In FIG. 3B, the tubing is illustrated as having been slid down to register with a portion of the rings 48, providing an electrode which is adjustable along the axis of the lead by positioning of the window.

Figure 4:
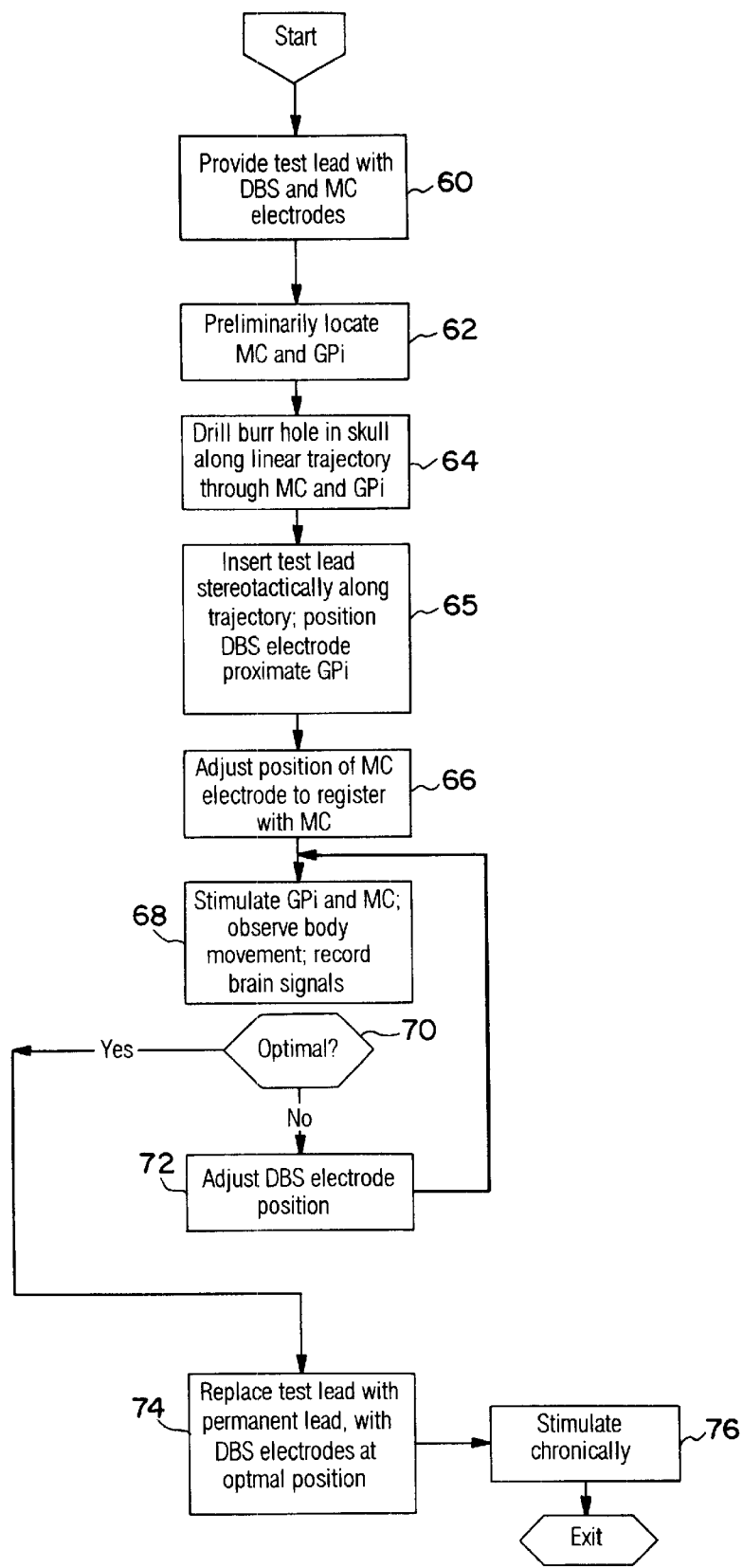

Referring now to FIG. 4, there is illustrated a flow diagram of the primary steps taken in carrying out the procedure of this invention, illustrated with respect to the MC/GPi embodiment. At block 60, the test is initiated by providing a test lead as discussed in connection with FIGS. 2 through 3B above. Such a test lead is provided with respective MC and GPi electrodes, where the position of the MC electrode is preferably adjustable to account for required patient variations in inter-electrode distance, as discussed in connection with FIG. 1. The location of the GPi and the MC are then preliminarily determined, as indicated at 62. The approximate location of the GPi can be determined non-invasively; a more exact location of the GPi target can be determined as discussed in the above referenced U.S. patent application Ser. No. 09/009,247. The location of the MC can be determined, e.g., by trans-cranial magnetic stimulation. With this information having been obtained, the desired one-dimensional trajectory through the two targets is known. Next, at 64, a burr hole is drilled to provide entry through the skull for the desired linear trajectory. Note that if a first burr hole is drilled in order to perform the initial localization, it can be used for placement of a separate lead to the GPi, as discussed above. Then, as indicated at 65, the test lead is stereotactically introduced along the trajectory, and the distal DBS electrode positioned in the area of the GPi. After that, at 66, the position of the MC electrode 44 is adjusted, e.g., in the manner suggested by the discussion of FIGS. 3A, B. The positioning of electrode 44 with respect to the MC will, of course, depend upon what body portion is to be tested or treated. After this, at 68, the two targets are stimulated, and the relevant body movement, or lack thereof, is noted. This provides the feedback for determining when the DBS electrode has been optimally located. Also, at 68, brain activity at the two sites can be recorded.

At 70, it is determined whether the DBS electrode complex 46 is optimally located. If no, which would include a state of uncertainty, the position of the DBS electrode is adjusted, as shown at 72, and then the stimulation is repeated, as indicated by the branch that loops back to 68. When the physician is satisfied that an optimal position has been found, the test is concluded, and the permanent lead is implanted, as indicated at 74. The lead is then attached to the generator device, and the patient is chronically stimulated, as indicated at 76. As mentioned above, by providing a permanent lead that also has an MC electrode, and is placed along the trajectory that encompasses both targets, subsequent tests can be conducted. Further, brain signal recordings can be obtained from the electrode sites, either concurrently, or at one site during stimulation of the other site.

There is thus provided a system and method for stimulating or recording at dual sites in a patient's brain, e.g., a feedback site such as the motor cortex, and a deep brain or neuro-modulation site such as the GPi. While the preferred embodiment has been presented as a single lead, either a test or permanent lead, it is to be understood that the invention can likewise be practiced by insertion of two leads, e.g., one for positioning of an electrode at the motor cortex and one for positioning of an electrode at the GPi. As used herein, the term "electrode" means either a single electrode or a plurality of electrodes, as illustrated in FIGS. 2 and 3A.

What is claimed is:

1. A method of testing to determine postioning of a brain stimulation lead for optimal deep brain stimulation to treat a movement disorder, said lead having MC electrode means for delivering stimulation to the motor cortex and DBS electrode means for delivering stimulation to a predetermined deep brain target, said method being carried out while said patient is under surgery for implantation of said lead, comprising:

positioning said lead along a substantially linear trajectory which includes both the patient's motor cortex and said predetermined deep brain target;

stimulating said motor cortex and said deep brain target concurrently, and observing movement of a predetermined body part corresponding to said disorder; and adjusting said lead to stimulate said deep brain target at a location which provides optimal stimulation for movement of said body part.

2. The method as described in claim 1, wherein said positioning comprises positioning said MC electrode means in the area of the patient's motor cortex and positioning said DBS electrode means in the area of said patient's deep brain target.

3. The method as described in claim 1, comprising providing said lead with a first electrode for delivering stimulus pulses to the patient's motor cortex, said providing including adjusting the position of said electrode relative to the DBS electrode.

4. The method as described in claim 1, comprising first determining approximately a linear trajectory that encompasses both said motor cortex and said deep brain target, and drilling a burr hole in the patient's skull along said trajectory.

5. The method as described in claim 1, comprising inserting said lead stereotactically along said trajectory.

6. The method as described in claim 1, comprising selecting the GPi as said deep brain target.

7. A method of testing to determine the optimal location of a deep brain target for stimulation of said target so as to treat a neurological disorder affecting a body part, said method comprising use of test lead means for delivering respective stimulation to a predetermined patient feedback target as well as to said deep brain target, comprising:

positioning said test lead means within a patient's skull so that stimulation can be delivered concurrently to each of said targets;

generating first stimulation pulses and connecting said first stimulation pulses to said test lead means so as to stimulate said feedback target, and concurrently generating DBS stimulation pulses and connecting said DBS stimulation pulses to said test lead means so as to stimulate said deep brain target;

determining the movement of said body part during said concurrent stimulating;

adjusting the position of said lead means relative to said deep brain target, so as to change the efficiency of stimulation of said deep brain target, and observing the resulting movement of said body part; and determining the optimal deep brain target location by determining when said concurrent stimulation evokes the best response of said body part.

8. The method as described in claim 7, comprising providing a single lead having MC electrode means positioned thereon for stimulating said motor cortex and DBS electrode means positioned thereon for stimulating said deep brain target, and inserting said lead into said patient's head along a substantially linear trajectory for stimulating said motor cortex and said target.

9. The method as described in claim 7, comprising providing a first lead having MC electrode means positioned thereon for stimulating said motor cortex and inserting said first lead into said patient's head so as to position said MC electrode means at said motor cortex, and providing a second lead having deep brain electrode means positioned thereon for stimulating said deep brain target and inserting said second lead into said patient's head so as to position said deep brain electrode means at said deep brain target.

* * * * *

UNITED STATES PATENT AND TRADEMARK OFFICE
CERTIFICATE OF CORRECTION

PATENT NO. : 6,484,059 B2
APPLICATION NO. : 09/799709
DATED : November 19, 2002
INVENTOR(S) : Frans L. H. Gielen It is certified that error appears in the above-identified patent and that said Letters Patent is hereby corrected as shown below:

Title page, item [54] and col. 1

TITLE: "METHOD FOR OPTIMIZED BRIAN STIMULATION FOR TREATING MOVEMENT DISORDERS" should read --METHOD FOR OPTIMIZED BRAIN STIMULATION--

Signed and Sealed this

Eighteenth Day of November, 2008

JON W. DUDAS
*Director of the United States Patent and Trademark Office*